US012715956B2

(12) United States Patent
Usui et al.

(10) Patent No.: US 12,715,956 B2
(45) Date of Patent: Aug. 25, 2026

(54) WATER-DISPERSIBLE POLYISOCYANATE, AQUEOUS POLYURETHANE RESIN COMPOSITION, AND ARTICLE

(71) Applicant: MITSUI CHEMICALS, INC., Tokyo (JP)

(72) Inventors: Yuta Usui, Shizuoka (JP); Koji Takamatsu, Shizuoka (JP); Kazuyuki Fukuda, Ichihara (JP); Yohei Koyama, Tokyo (JP); Tatsuya Shibata, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 766 days.

(21) Appl. No.: 18/246,067

(22) PCT Filed: Sep. 29, 2021

(86) PCT No.: PCT/JP2021/035760
§ 371 (c)(1),
(2) Date: Mar. 21, 2023

(87) PCT Pub. No.: WO2022/071361
PCT Pub. Date: Apr. 7, 2022

(65) Prior Publication Data

US 2023/0357485 A1 Nov. 9, 2023

(30) Foreign Application Priority Data

Sep. 30, 2020 (JP) ................................ 2020-165601

(51) Int. Cl.

| | |
|---|---|
| ***C08G 18/75*** | (2006.01) |
| ***C07C 265/14*** | (2006.01) |
| ***C08G 18/40*** | (2006.01) |
| ***C08G 18/42*** | (2006.01) |
| ***C08G 18/78*** | (2006.01) |
| ***C08G 18/79*** | (2006.01) |
| ***C08G 18/80*** | (2006.01) |
| ***C09D 175/06*** | (2006.01) |
| ***C09D 175/08*** | (2006.01) |

(52) U.S. Cl.
CPC .......... *C08G 18/757* (2013.01); *C07C 265/14* (2013.01); *C08G 18/4018* (2013.01); *C08G 18/4238* (2013.01); *C08G 18/7806* (2013.01); *C08G 18/79* (2013.01); *C08G 18/80* (2013.01); *C09D 175/06* (2013.01); *C09D 175/08* (2013.01)

(58) Field of Classification Search
None
See application file for complete search history.

(56) References Cited

U.S. PATENT DOCUMENTS

| | | | | |
|---|---|---|---|---|
| 2004/0034162 | A1 | 2/2004 | Laas et al. | |
| 2009/0156738 | A1 | 6/2009 | Laas et al. | |
| 2010/0216905 | A1* | 8/2010 | Kuwamura | ........ C08G 18/6659 528/65 |
| 2018/0155574 | A1 | 6/2018 | Laas et al. | |
| 2019/0330408 | A1 | 10/2019 | Laas | |
| 2019/0330409 | A1 | 10/2019 | Laas | |
| 2021/0130530 | A1 | 5/2021 | Laas et al. | |

FOREIGN PATENT DOCUMENTS

| | | | | |
|---|---|---|---|---|
| EP | 3560975 | A1 | 10/2019 | |
| JP | 2003-533566 | A | 11/2003 | |
| JP | 2013-67721 | A | 4/2013 | |
| JP | 2018-513239 | A | 5/2018 | |
| JP | 2019189866 | A * | 10/2019 | ........... C08G 18/792 |
| WO | 2020/016116 | A1 | 1/2020 | |

* cited by examiner

*Primary Examiner* — Robert S Jones, Jr.
*Assistant Examiner* — Lily K Sloan
(74) *Attorney, Agent, or Firm* — RANKIN, HILL & CLARK LLP

(57) ABSTRACT

A water-dispersible polyisocyanate contains an isocyanate group and a sulfone group. The water-dispersible polyisocyanate contains a reaction product of a polyisocyanate component and a hydrophilic active hydrogen component. The polyisocyanate component contains a bis(isocyanatomethyl)cyclohexane derivative. The hydrophilic active hydrogen component contains a sulfone group-containing active hydrogen compound. The bis(isocyanatomethyl)cyclohexane derivative contains an allophanate derivative and an isocyanurate derivative. The allophanate derivative is contained in an amount of 25% by mass or more and 75% by mass or less relative to the total amount of the allophanate derivative and the isocyanurate derivative.

6 Claims, No Drawings

WATER-DISPERSIBLE POLYISOCYANATE, AQUEOUS POLYURETHANE RESIN COMPOSITION, AND ARTICLE

TECHNICAL FIELD

The present invention relates to a water-dispersible polyisocyanate, an aqueous polyurethane resin composition, and an article.

BACKGROUND ART

Polyurethane resins are widely used in various industrial fields. The polyurethane resin is a reaction product of a polyisocyanate component and a polyol component.

The polyisocyanate component is prepared for use as, for example, an organic solvent solution. In recent years, in order to improve environmental friendliness and workability, it has been demanded to prepare the polyisocyanate component in the form of an aqueous dispersion. That is, the polyisocyanate component has been demanded to be dispersible in water.

As the polyisocyanate component that is dispersible in water, the following has been proposed. Specifically, a polyisocyanate mixture obtained by reaction of isocyanurate of pentamethylene 1,5-diisocyanate with 3-(cyclohexylamino)propanesulfonic acid (cf. Patent Document 1 (Example 5)).

As the polyisocyanate component that is dispersible in water, the following has also been proposed. Specifically, a polyisocyanate mixture obtained by reaction of isocyanurate of hexamethylene 1,6-diisocyanate with 3-(cyclohexylamino)propanesulfonic acid (cf. Patent Document 2 (Example 1)).

Further, as the polyisocyanate component that is dispersible in water, the following has also been proposed. Specifically, a polyisocyanate mixture obtained by reaction of isocyanurate of 1-isocyanato-3,3,5-trimethyl-5-isocyanatomethylcyclohexane with 3-(cyclohexylamino)propanesulfonic acid (cf. Patent Document 2 (Example 5)).

The above-described polyisocyanate mixture is water-dispersible by a sulfone group of 3-(cyclohexylamino)propanesulfonic acid. A polyurethane resin is obtained by reaction of the above-described polyisocyanate mixture with a polyol component.

CITATION LIST

Patent Documents

Patent Document 1: Japanese Unexamined Patent Application Publication (Translation of PCT Application) No. 2018-513239

Patent Document 2: Japanese Unexamined Patent Application Publication (Translation of PCT Application) No. 2003-533566

SUMMARY OF THE INVENTION

Problem to be Solved by the Invention

However, when pentamethylene 1,5-diisocyanate and/or its derivative is/are dispersed in water by a sulfone group, hardness of the polyurethane resin decreases.

Also, when hexamethylene 1,6-diisocyanate and/or its derivative is/are dispersed in water by a sulfone group, hardness of the polyurethane resin decreases.

Further, when 1-isocyanato-3,3,5-trimethyl-5-isocyanatomethylcyclohexane and/or its derivative is/are dispersed in water by a sulfone group, curability of the polyurethane resin decreases.

The present invention provides a water-dispersible polyisocyanate, an aqueous polyurethane resin composition, and an article that can obtain a polyurethane resin having excellent hardness and that have excellent curability and water dispersibility.

Means for Solving the Problem

The present invention [1] includes a water-dispersible polyisocyanate being a water-dispersible polyisocyanate containing an isocyanate group and a sulfone group, containing a reaction product of a polyisocyanate component and a hydrophilic active hydrogen component, the polyisocyanate component containing a bis(isocyanatomethyl)cyclohexane derivative, the hydrophilic active hydrogen component containing a sulfone group-containing active hydrogen compound, the bis(isocyanatomethyl)cyclohexane derivative containing an allophanate derivative and an isocyanurate derivative, in which the allophanate derivative is contained in an amount of 25% by mass or more and 75% by mass or less relative to a total amount of the allophanate derivative and the isocyanurate derivative.

The present invention [2] includes the water-dispersible polyisocyanate described in [1], in which the bis(isocyanatomethyl)cyclohexane derivative contains a reaction product of a bis(isocyanatomethyl)cyclohexane monomer and an alcohol, and the alcohol contains a monool.

The present invention [3] includes the water-dispersible polyisocyanate described in [1] or [2], in which the sulfone group is contained in an amount of 0.2% by mass or more and 5% by mass or less relative to a total amount of the water-dispersible polyisocyanate.

The present invention [4] includes the water-dispersible polyisocyanate described in any one of the above-described [1] to [3], in which the isocyanate group of the water-dispersible polyisocyanate is blocked with a blocking agent.

The present invention [5] includes an aqueous polyurethane resin composition containing the water-dispersible polyisocyanate described in any one of the above-described [1] to [4]; and an active hydrogen group-containing compound.

The present invention [6] includes an article, including a coated object; and a polyurethane layer disposed on a surface of the coated object, in which the polyurethane layer contains a cured coating film of the aqueous polyurethane resin composition according to claim 5.

Effects of the Invention

The water-dispersible polyisocyanate of the present invention contains a reaction product of a polyisocyanate component containing a bis(isocyanatomethyl)cyclohexane derivative and a hydrophilic active hydrogen component containing a sulfone group-containing active hydrogen compound. The bis(isocyanatomethyl)cyclohexane derivative contains an allophanate derivative and an isocyanurate derivative, and has an allophanate derivative content ratio within a predetermined range.

Therefore, the water-dispersible polyisocyanate of the present invention can obtain a polyurethane resin having excellent hardness and has excellent curability and water dispersibility.

The aqueous polyurethane resin composition of the present invention contains the above-described water-dispersible polyisocyanate. Therefore, the aqueous polyurethane resin composition of the present invention can obtain a polyurethane resin having excellent hardness and is excellent in curability.

The article of the present invention has a polyurethane layer having excellent hardness because it includes a cured coating film of the above-described aqueous polyurethane resin composition.

DESCRIPTION OF THE EMBODIMENTS

The water-dispersible polyisocyanate of the present invention contains an isocyanate group and a sulfone group. The water-dispersible polyisocyanate is a polyisocyanate that can be dispersed in water.

The water-dispersible polyisocyanate of the present invention contains a reaction product of a polyisocyanate component and a hydrophilic active hydrogen component.

The polyisocyanate component contains a bis(isocyanatomethyl)cyclohexane derivative as an essential component.

The bis(isocyanatomethyl)cyclohexane derivative has an allophanate derivative of bis(isocyanatomethyl)cyclohexane and an isocyanurate derivative of bis(isocyanatomethyl) cyclohexane.

Such a bis(isocyanatomethyl)cyclohexane derivative is, for example, a reaction product of a bis(isocyanatomethyl) cyclohexane monomer and an alcohol. More specifically, the bis(isocyanatomethyl)cyclohexane derivative is produced by, for example, the following method. In this method, first, a bis(isocyanatomethyl)cyclohexane monomer is allowed to react with an alcohol.

Examples of the bis(isocyanatomethyl)cyclohexane monomer include 1,2-bis(isocyanatomethyl)cyclohexane, 1,3-bis(isocyanatomethyl)cyclohexane, and 1,4-bis(isocyanatomethyl)cyclohexane.

These bis(isocyanatomethyl)cyclohexane monomers can be used alone or in combination of two or more.

For the bis(isocyanatomethyl)cyclohexane monomer, preferably, 1,3-bis(isocyanatomethyl)cyclohexane and 1,4-bis(isocyanatomethyl)cyclohexane are used, more preferably, 1,3-bis(isocyanatomethyl)cyclohexane is used.

Examples of the alcohol include monool, diol, and triol.

Examples of the monool include linear monohydric alcohol and branched monohydric alcohol.

Examples of the linear monohydric alcohol include methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, n-pentadecanol, n-hexadecanol, n-heptadecanol, n-octadecanol, n-nonadecanol, and eicosanol. These can be used alone or in combination of two or more.

Examples of the branched monohydric alcohol include isopropanol, isobutanol (isobutyl alcohol), sec-butanol, tert-butanol, isopentanol, isohexanol, isoheptanol, isooctanol, 2-ethylhexane-1-ol, isononanol, isodecanol, 5-ethyl-2-nonanol, trimethylnonyl alcohol, 2-hexyldecanol, 3,9-diethyl-6-tridecanol, 2-isoheptylisoundecanol, and 2-octyldodecanol. These can be used alone or in combination of two or more. These monools can be used alone or in combination of two or more.

Examples of the diol include linear dihydric alcohol and branched dihydric alcohol.

Examples of the linear dihydric alcohol include linear alkanediol. Examples of the linear alkanediol include ethylene glycol, 1,3-propanediol, 1,4-butanediol (1,4-butylene glycol), 1,5-pentanediol, 1,6-hexanediol, 1,4-dihydroxy-2-butene, diethylene glycol, triethylene glycol, and dipropylene glycol. These can be used alone or in combination of two or more.

Examples of the branched dihydric alcohol include branched alkanediol. Examples of the branched alkanediol include 1,2-propanediol, 1,3-butanediol, 1,2-butylene glycol, neopentyl glycol, 3-methyl-1,5-pentanediol, 2,2,2-trimethylpentanediol, 3,3-dimethylolheptane, and 2,6-dimethyl-1-octene-3,8-diol. These can be used alone or in combination of two or more.

These diols can be used alone or in combination of two or more.

Examples of the triol include glycerin, trimethylolpropane, and triisopropanolamine. These can be used alone or in combination of two or more.

These triols can be used alone or in combination of two or more.

These alcohols can be used alone or in combination of two or more.

The alcohol has, for example, 1 or more carbon atoms, preferably 2 or more carbon atoms. The alcohol also has, for example, 50 or less carbon atoms, preferably 40 or less carbon atoms, more preferably 30 or less carbon atoms, even more preferably 20 or less carbon atoms, further preferably 10 or less carbon atoms, particularly preferably 4 or less carbon atoms.

When the number of carbon atoms in the alcohol is within the above-described range, water dispersibility of the bis(isocyanatomethyl)cyclohexane derivative can be improved.

For the alcohol, preferably, monool is used, more preferably, branched monohydric alcohol is used, further preferably, isobutanol is used. By using these alcohols, the water dispersibility of the bis(isocyanatomethyl)cyclohexane derivative can be improved.

The amounts of the bis(isocyanatomethyl)cyclohexane monomer and the alcohol blended are appropriately set without inhibiting the excellent effect of the present invention.

More specifically, an equivalent ratio (NCO/OH) of the isocyanate group of the bis(isocyanatomethyl)cyclohexane monomer to the hydroxyl group of the alcohol is, for example, more than 1, preferably 5 or more, more preferably 10 or more. Further, the equivalent ratio (NCO/OH) of the isocyanate group of the bis(isocyanatomethyl)cyclohexane monomer to the hydroxyl group of the alcohol is, for example, 1000 or less, preferably 600 or less, more preferably 500 or less, further preferably 100 or less.

The alcohol is blended in an amount of, for example, 3 parts by mass or more, preferably 3.2 parts by mass or more, more preferably 3.5 parts by mass or more relative to 100 parts by mass of the bis(isocyanatomethyl)cyclohexane monomer. The alcohol is blended in an amount of, for example, 50 parts by mass or less, preferably 20 parts by mass or less, more preferably 10 parts by mass or less relative to 100 parts by mass of the bis(isocyanatomethyl) cyclohexane monomer.

The reaction conditions of the bis(isocyanatomethyl)cyclohexane monomer and the alcohol are appropriately set without inhibiting the excellent effect of the present invention. More specifically, the reaction conditions include environmental conditions of inert atmosphere and normal pressure. Further, the reaction temperature is, for example, 20° C. or more, preferably 40° C. or more. The reaction temperature is, for example, 100° C. or less, preferably 90° C. or less. The reaction time is, for example, 0.05 hours or more, preferably 0.2 hours or more. Further, the reaction time is, for example, 10 hours or less, preferably 6 hours or less.

In this method, as necessary, a urethanizing catalyst can be blended with the bis(isocyanatomethyl)cyclohexane monomer and the alcohol. Examples of the urethanizing catalyst include known amines and known organic metallic compounds. The blending amount of the urethanizing catalyst is not particularly limited and is appropriately set in accordance with its purpose and use.

In this manner, the bis(isocyanatomethyl)cyclohexane monomer and the alcohol are subjected to urethane-forming reaction. As a result of this, a urethanization reaction product is obtained.

Then, in this method, the urethanization reaction product is subjected to allophanate-forming reaction and isocyanurate-forming reaction.

More specifically, in this method, an allophanate/isocyanurate-forming catalyst is blended with the urethanization reaction product and heated.

The allophanate/isocyanurate-forming catalyst is not particularly limited as long as it is a catalyst capable of accelerating allophanate formation and isocyanurate formation of the isocyanate group. Examples of the allophanate/isocyanurate-forming catalyst include tertiary amine, Mannich base, Friedel-Crafts catalyst, metal salt of alkyl carboxylic acid, organic metallic compound, halogen-substituted organic phosphorus compound, tetraalkylammonium hydroxide, organic weak acid salt of tetraalkylammonium, trialkylhydroxyalkylammonium hydroxide, and organic weak acid salt of trialkylhydroxyalkylammonium. These can be used alone or in combination of two or more.

For the allophanate/isocyanurate-forming catalyst, preferably, an organic weak acid salt of trialkylhydroxyalkylammonium is used.

Examples of the trialkylhydroxyalkylammonium include N-(2-hydroxypropyl)-N,N,N-trimethylammonium, trimethylhydroxyethylammonium, triethylhydroxypropylammonium, and triethylhydroxyethylammonium. These can be used alone or in combination of two or more.

Examples of the organic weak acid salt include acetic acid salt, propionic acid salt, 2-ethylhexanoic acid salt, octyl acid salt, capric acid salt, myristic acid salt, benzoic acid salt. These can be used alone or in combination of two or more.

The allophanate/isocyanurate-forming catalyst is blended in an amount of, for example, 0.0005 parts by mass or more, preferably 0.001 parts by mass or more relative to 100 parts by mass of the bis(isocyanatomethyl)cyclohexane monomer. Further, the allophanate/isocyanurate-forming catalyst is blended in an amount of, for example, 0.3 parts by mass or less, preferably 0.05 parts by mass or less, more preferably 0.03 parts by mass or less relative to 100 parts by mass of the bis(isocyanatomethyl)cyclohexane monomer.

The reaction conditions for the allophanate-forming reaction and the isocyanurate-forming reaction are appropriately set without inhibiting the excellent effect of the present invention. More specifically, the reaction conditions include environmental conditions of inert atmosphere and normal pressure. Further, the reaction temperature is, for example, 0° C. or more, preferably 20° C. or more. The reaction temperature is, for example, 160° C. or less, preferably 120° C. or less. The reaction time is, for example, 30 minutes or more, preferably 60 minutes or more.

Further, the reaction time is, for example, 20 hours or less, preferably 10 hours or less.

Once a reaction rate (isocyanate group conversion) of the reaction solution reaches a predetermined value, a reaction inhibitor is added to the reaction solution. The isocyanate group conversion at the time of stopping the reaction is, for example, 1% by mass or more, preferably 5% by mass or more. Further, the isocyanate group conversion at the time of stopping the reaction is, for example, 20% by mass or less, preferably 15% by mass or less. The isocyanate group conversion can be calculated by a known method.

Examples of the reaction inhibitor include phosphoric acid, monochloroacetic acid, benzoyl chloride, dodecylbenzenesulfonic acid, o-toluenesulfonic acid, p-toluenesulfonic acid, methyl o-toluenesulfonate, methyl p-toluenesulfonate, o-toluenesulfoneamide, and p-toluenesulfoneamide. These can be used alone or in combination of two or more. The blending amount of the reaction inhibitor is appropriately set in accordance with its purpose and use.

A catalyst adsorbent may be added in place of the reaction inhibitor. Examples of the catalyst adsorbent include chelate resin and ion exchange resin. These can be used alone or in combination of two or more. The blending amount of the catalyst adsorbent is appropriately set in accordance with its purpose and use.

In this manner, the allophanate-forming reaction and the isocyanurate-forming reaction are stopped.

As a result of this, a composition containing an allophanate derivative of bis(isocyanatomethyl)cyclohexane and an isocyanurate derivative of bis(isocyanatomethyl)cyclohexane is obtained as the reaction product.

In each of the above-described reactions, an auxiliary catalyst can be blended. Examples of the auxiliary catalyst include known organic phosphite esters. For the organic phosphite ester, preferably, monophosphites are used, more preferably, tris(tridecyl)phosphite is used.

The auxiliary catalyst is blended in an amount of, for example, 0.01 parts by mass or more, preferably 0.02 parts by mass or more, more preferably 0.03 parts by mass or more relative to 100 parts by mass of the bis(isocyanatomethyl)cyclohexane monomer. Further, the auxiliary catalyst is blended in an amount of, for example, 0.2 parts by mass or less, preferably 0.15 parts by mass or less, more preferably 0.1 parts by mass or less relative to 100 parts by mass of the bis(isocyanatomethyl)cyclohexane monomer.

In each of the above-described reactions, a reaction stabilizer can be added. Examples of the reaction stabilizer include known hindered phenol antioxidants. For the reaction stabilizer, preferably, 2,6-di(tert-butyl)-4-methylphenol (BHT) is used.

The reaction stabilizer is blended in an amount of, for example, 0.01 parts by mass or more, preferably 0.05 parts by mass or more relative to 100 parts by mass of the bis(isocyanatomethyl)cyclohexane monomer.

Further, the reaction stabilizer is blended in an amount of, for example, 1.0 part by mass or less, preferably 0.10 parts by mass or less relative to 100 parts by mass of the bis(isocyanatomethyl)cyclohexane monomer.

In each of the above-described reactions, a known reaction solvent can be added. The blending amount of the reaction solvent is appropriately set in accordance with its purpose and use. In each of the above-described reactions, the reaction solution can be purified. Examples of the purification method include distillation and extraction. The purification removes unreacted bis(isocyanatomethyl)cyclohexane monomer from the reaction solution. Further, the urethanizing catalyst, the isocyanurate-forming catalyst, a catalyst deactivator, the auxiliary catalyst, the reaction stabilizer, and/or the reaction solvent are removed together with the bis(isocyanatomethyl)cyclohexane monomer.

In the above-described reaction, the bis(isocyanatomethyl)cyclohexane is allophanate-modified and isocyanurate-modified.

That is, in the above-described reaction, an allophanate derivative of bis(isocyanatomethyl)cyclohexane and an isocyanurate derivative of bis(isocyanatomethyl)cyclohexane are formed.

In the bis(isocyanatomethyl)cyclohexane derivative, the allophanate derivative is contained in an amount of, for example, 25% by mass or more, preferably 30% by mass or more, more preferably 35% by mass or more, further preferably 40% by mass or more, particularly preferably 45% by mass or more relative to the total amount of the allophanate derivative and the isocyanurate derivative. Further, the allophanate derivative is contained in an amount of, for example, 75% by mass or less, preferably 70% by mass or less, more preferably 65% by mass or less, further preferably 60% by mass or less, particularly preferably 55% by mass or less relative to the total amount of the allophanate derivative and the isocyanurate derivative.

When the content ratio of the allophanate derivative is the above-described lower limit or more, a water-dispersible polyisocyanate having excellent curability and water dispersibility is obtained. When the content ratio of the allophanate derivative is the above-described upper limit or less, a polyurethane resin having excellent hardness is obtained.

The isocyanurate derivative is contained in an amount of, for example, 25% by mass or more, preferably 30% by mass or more, more preferably 35% by mass or more, further preferably 40% by mass or more, particularly preferably 45% by mass or more relative to the total amount of the allophanate derivative and the isocyanurate derivative. Further, the isocyanurate derivative is contained in an amount of, for example, 75% by mass or less, preferably 70% by mass or less, more preferably 65% by mass or less, further preferably 60% by mass or less, particularly preferably 55% by mass or less relative to the total amount of the allophanate derivative and the isocyanurate derivative.

When the content ratio of the isocyanate derivative is within the above-described range, a polyurethane resin having excellent hardness can be obtained, and a water-dispersible polyisocyanate having excellent curability and water dispersibility is obtained.

The content ratio of the allophanate derivative and the content ratio of the isocyanurate derivative are measured by a gel permeation chromatography in accordance with Examples to be described later.

In the above-described method, the allophanate derivative of bis(isocyanatomethyl)cyclohexane and the isocyanurate derivative of bis(isocyanatomethyl)cyclohexane are produced simultaneously. However, for example, the allophanate derivative of bis(isocyanatomethyl)cyclohexane and the isocyanurate derivative of bis(isocyanatomethyl)cyclohexane may be separately produced and then mixed at the above-described ratios. Further, the allophanate derivative of bis(isocyanatomethyl)cyclohexane and/or the isocyanurate derivative of bis(isocyanatomethyl)cyclohexane may be added to the above-described bis(isocyanatomethyl)cyclohexane derivative to adjust their contents to the above-described ratios.

The polyisocyanate component can contain other polyisocyanates as optional components.

Other polyisocyanates are polyisocyanates except the bis(isocyanatomethyl)cyclohexane derivative.

More specifically, for other polyisocyanates, bis(isocyanatomethyl)cyclohexane monomers are used.

For other polyisocyanates, widely industrially used polyisocyanates are also used. Examples of the widely industrially used polyisocyanate include aromatic polyisocyanate, araliphatic polyisocyanate, aliphatic polyisocyanate, and alicyclic polyisocyanate (except bis(isocyanatomethyl)cyclohexane). The widely industrially used polyisocyanate includes the same kind of derivatives as described above.

Other polyisocyanates can be used alone or in combination of two or more.

Such other polyisocyanates are contained in an amount of, for example, 90% by mass or less, preferably 70% by mass or less, more preferably 50% by mass or less, even more preferably 30% by mass or less, further preferably 10% by mass or less, particularly preferably 0% by mass relative to the total amount of the polyisocyanate component.

Specifically, the polyisocyanate component preferably consists of the bis(isocyanatomethyl)cyclohexane derivative and does not contain other polyisocyanates.

When the polyisocyanate component consists of the bis(isocyanatomethyl)cyclohexane derivative, a polyurethane resin having particularly excellent hardness can be obtained, and a water-dispersible polyisocyanate having excellent curability and water dispersibility is obtained.

The polyisocyanate component may be dissolved in a known organic solvent. In such a case, the polyisocyanate component has a solids concentration of, for example, 10% by mass or more, preferably 20% by mass or more. Further, the polyisocyanate component has a solids concentration of, for example, 90% by mass or less, preferably 80% by mass or less.

The above-described polyisocyanate component is then allowed to react with a hydrophilic active hydrogen component to be described later, to thereby obtain a water-dispersible polyisocyanate.

More specifically, in the preparation of the water-dispersible polyisocyanate, the polyisocyanate component is allowed to react with the hydrophilic active hydrogen component at a ratio at which free isocyanate groups remain.

The hydrophilic active hydrogen component contains a sulfone group-containing active hydrogen compound.

The sulfone group-containing active hydrogen compound is a compound containing one or more sulfone groups and one or more active hydrogen groups. Examples of the active hydrogen group include a hydroxyl group and an amino group.

For the sulfone group-containing active hydrogen compound, for example, a compound having both one active hydrogen group and one sulfone group is used. Examples of such a sulfone group-containing active hydrogen compound include hydroxyalkanesulfonic acid and aminosulfonic acid.

Examples of the hydroxyalkanesulfonic acid include hydroxymethanesulfonic acid, hydroxyethanesulfonic acid, and 3-hydroxypropanesulfonic acid. These can be used alone or in combination of two or more.

Examples of the aminosulfonic acid include 2-(cyclohexylamino)-ethanesulfonic acid (CHES) and 3-(cyclohexylamino)-propanesulfonic acid (CAPS). These can be used alone or in combination of two or more.

These sulfone group-containing active hydrogen compounds can be used alone or in combination of two or more.

For the sulfone group-containing active hydrogen compound, preferably, aminosulfonic acid is used, more preferably, 3-(cyclohexylamino)-propanesulfonic acid is used.

The hydrophilic active hydrogen component can contain other water-dispersible active hydrogen compounds as optional components.

Other water-dispersible active hydrogen compounds are water-dispersible active hydrogen compounds except the sulfone group-containing active hydrogen compound.

For other water-dispersible active hydrogen compounds, more specifically, a nonion group-containing active hydrogen compound, a carboxyl group-containing active hydrogen compound, and a phosphoric acid group-containing active hydrogen compound are used.

Examples of the nonion group-containing active hydrogen compound include polyoxyethylene compounds.

For the polyoxyethylene compound, for example, a compound having both an active hydrogen group and at least three consecutive ethylene oxide groups is used. Examples of such a polyoxyethylene compound include one-end-capped polyoxyethylene glycols and polyoxyethylene side chain-containing diols.

Examples of the one-end-capped polyoxyethylene glycol include alkoxypolyoxyethylene glycol of which one end is capped with an alkyl group having 1 to 20 carbon atoms. More specifically, methoxypolyoxyethylene glycol and ethoxypolyoxyethylene glycol are used. The one-end-capped polyoxyethylene glycol can be produced by a known method.

Examples of the polyoxyethylene side chain-containing diol include reaction products of polyoxyethylene group-containing monoisocyanate and dialkanolamine. The polyoxyethylene side chain-containing diol can be produced by a known method.

These polyoxyethylene compounds can be used alone or in combination of two or more.

The polyoxyethylene compound has a number average molecular weight of, for example, 200 or more, preferably 300 or more, and for example, 2000 or less, preferably 1000 or less.

The carboxyl group-containing active hydrogen compound is a compound having both an active hydrogen group and a carboxyl group. For the carboxyl group-containing active hydrogen compound, for example, a carboxyl group-containing active hydrogen compound having both one active hydrogen group and one carboxyl group is used. For the carboxyl group-containing active hydrogen compound, for example, a carboxyl group-containing active hydrogen compound having both two active hydrogen groups and one carboxyl group is also used.

Examples of the carboxyl group-containing active hydrogen compound having both one active hydrogen group and one carboxyl group include glycolic acid, lactic acid, hydroxypivalic acid, malic acid, and citric acid.

Examples of the carboxyl group-containing active hydrogen compound having both two active hydrogen groups and one carboxyl group include 2,2-dimethylolacetic acid, 2,2-dimethylollactic acid, 2,2-dimethylolpropionic acid, 2,2-dimethylolbutanoic acid, dimethylolheptanoic acid, dimethylolnonanoic acid, 2,2-dimethylolbutyric acid, and 2,2-dimethylolvaleric acid.

These carboxyl group-containing active hydrogen compounds can be used alone or in combination of two or more.

The phosphoric acid group-containing active hydrogen compound is a compound having both an active hydrogen group and a phosphoric acid group.

For the phosphoric acid group-containing active hydrogen compound, for example, a phosphoric acid group-containing active hydrogen compound having both one active hydrogen group and one phosphoric acid group is used.

Examples of such a phosphoric acid group-containing active hydrogen compound include hydroxyalkylphosphonic acids and aminoalkylphosphonic acids.

These phosphoric acid group-containing active hydrogen compounds can be used alone or in combination of two or more.

Other water-dispersible active hydrogen compounds can be used alone or in combination of two or more.

Other water-dispersible active hydrogen compounds are contained in an amount of, for example, 90% by mass or less, preferably 70% by mass or less, more preferably 50% by mass or less, even more preferably 30% by mass or less, further preferably 10% by mass or less, particularly preferably 0% by mass relative to the total amount of the hydrophilic active hydrogen component.

Specifically, the hydrophilic active hydrogen component particularly preferably consists of a sulfone group-containing active hydrogen compound, and does not contain other water-dispersible active hydrogen compounds.

When the hydrophilic active hydrogen component consists of a sulfone group-containing active hydrogen compound, a polyurethane resin having particularly excellent hardness and mechanical properties can be obtained, and a water-dispersible polyisocyanate having excellent curability and water dispersibility is obtained.

The reaction ratio of the polyisocyanate component and the hydrophilic active hydrogen component is adjusted so that free isocyanate groups remain in the reaction product.

More specifically, an equivalent ratio (active hydrogen group/NCO) of the active hydrogen group of the hydrophilic active hydrogen component to the isocyanate group of the polyisocyanate component is, for example, 0.30 or less, preferably 0.20 or less. Further, the equivalent ratio (active hydrogen group/NCO) of the active hydrogen group of the hydrophilic active hydrogen component to the isocyanate group of the polyisocyanate component is, for example, 0.01 or more, preferably 0.10 or more.

The hydrophilic active hydrogen component is blended in an amount of, for example, 10 parts by mass or more, preferably 20 parts by mass or more, more preferably 25 parts by mass or more relative to 100 parts by mass of the polyisocyanate component. Further, the hydrophilic active hydrogen component is blended in an amount of, for example, 70 parts by mass or less, preferably 60 parts by mass or less, more preferably 55 parts by mass or less relative to 100 parts by mass of the polyisocyanate component.

The reaction conditions of the polyisocyanate component and the hydrophilic active hydrogen component are appropriately set without inhibiting the excellent effect of the present invention. More specifically, the reaction conditions include environmental conditions of inert atmosphere and normal pressure. Further, the reaction temperature is, for example, 50° C. or more, preferably 70° C. or more. The reaction temperature is, for example, 150° C. or less, preferably 110° C. or less. The reaction time is, for example, 0.5 hours or more, preferably 1 hour or more. Further, the reaction time is, for example, 120 hours or less, preferably 72 hours or less.

Completion of the reaction is confirmed by, for example, checking if the isocyanate amount in the reaction solution no longer changes. The isocyanate amount is measured by titration or infrared absorption.

In this method, preferably, a neutralizing agent is added to the reaction solution to form a salt of the sulfone group. Specifically, the sulfone group may or may not be a salt. Preferably, a salt of the sulfone group is used for the sulfone group.

For the neutralizing agent, a conventional base is used. For the base, specifically, an organic base and an inorganic base are used.

Examples of the organic base include tertiary amines and secondary amines. Examples of the tertiary amine include trialkylamine and alkanolamine. Examples of the trialkylamine include trimethylamine, triethylamine, and N,N-dimethylcyclohexylamine. Examples of the alkanolamine include dimethylethanolamine, methyldiethanolamine, triethanolamine, and triisopropanolamine. Examples of the secondary amine include heterocyclic amines. Examples of the heterocyclic amine include morpholine. These organic bases can be used alone or in combination of two or more.

Examples of the inorganic base include ammonia, alkali metal hydroxides, alkaline earth metal hydroxides, and alkali metal carbonates. Examples of the alkali metal hydroxide includes lithium hydroxide, sodium hydroxide, and potassium hydroxide. Examples of the alkaline earth metal hydroxide includes magnesium hydroxide and calcium hydroxide. Examples of the alkali metal carbonate includes sodium carbonate and potassium carbonate. These inorganic bases can be used alone or in combination of two or more.

These neutralizing agents can be used alone or in combination of two or more.

For the neutralizing agent, preferably, organic base is used, more preferably, tertiary amine is used, further preferably, trialkylamine is used, particularly preferably, N,N-dimethylcyclohexylamine is used.

The neutralizing agent is added in an amount of, for example, 0.4 equivalent weights or more, preferably 0.6 equivalent weights or more relative to 1 equivalent weight of the sulfone group. Further, the neutralizing agent is added in an amount of, for example, 1.2 equivalent weights or less, preferably 1.0 equivalent weight or less relative to 1 equivalent weight of the sulfone group.

In this manner, a water-dispersible polyisocyanate containing the isocyanate group and the sulfone group is obtained.

In the water-dispersible polyisocyanate, the isocyanate group may be a free isocyanate group. The isocyanate group may also be blocked with a blocking agent. Specifically, for the isocyanate group, a free isocyanate group and a blocked isocyanate group are used.

The blocking agent is a compound having an active group reactive with the isocyanate group (hereinafter referred to as a blocking group). Examples of the blocking agent include an active methylene compound, an active methine compound, an imidazole compound, an imidazoline compound, a pyrimidine compound, a guanidine compound, an alcohol compound, a phenol compound, an amine compound, an imine compound, an oxime compound, a carbamic acid compound, a urea compound, an acid amide compound, a lactam compound, an acid imide compound, a triazole compound, a pyrazole compound, a mercaptan compound, and a bisulfite. These can be used alone or in combination of two or more. For the blocking agent, preferably, an imidazole compound, an imidazoline compound, an oxime compound, and a pyrazole compound are used.

The water-dispersible polyisocyanate having free isocyanate groups is allowed to react with the above-described blocking agent, to thereby form a water-dispersible polyisocyanate having blocked isocyanate groups.

The blending amounts of the water-dispersible polyisocyanate having free isocyanate groups and the above-described blocking agent are adjusted, for example, based on the equivalent ratio of the blocking group in the blocking agent to the isocyanate group in the water-dispersible polyisocyanate.

More specifically, an equivalent ratio (blocking group/isocyanate group) of the blocking group to the free isocyanate group is, for example, 0.2 or more, preferably 0.5 or more, more preferably 0.8 or more, further preferably 1.0 or more. Further, the equivalent ratio (blocking group/isocyanate group) of the blocking group to the free isocyanate group is, for example, 1.5 or less, preferably 1.2 or less, more preferably 1.1 or less.

The reaction conditions of the water-dispersible polyisocyanate having free isocyanate groups and the above-described blocking agent are appropriately set without inhibiting the excellent effect of the present invention. More specifically, the reaction conditions include environmental conditions of inert atmosphere and normal pressure. Further, the reaction temperature is, for example, 0° C. or more, preferably 20° C. or more. The reaction temperature is, for example, 100° C. or less, preferably 80° C. or less, more preferably 70° C. or less. The reaction time is, for example, 0.5 hours or more, preferably 1.0 hour or more. Further, the reaction time is, for example, 24 hours or less, preferably 12 hours or less.

Completion of the reaction is confirmed by, for example, checking if the isocyanate amount in the reaction solution no longer changes. The isocyanate amount is measured by titration or infrared absorption.

All the above-described reactions may be performed in the absence of a solvent. Alternatively, all the above-described reactions may be performed in the presence of a solvent. Examples of the solvent include known organic solvents. The blending amount of the solvent is appropriately set in accordance with its purpose and use.

When used, the solvent can also be removed after completion of the reaction. Examples of the method for removing the solvent include distillation and extraction.

In the following, the isocyanate group refers to a free isocyanate group and an isocyanate group that has been blocked with a blocking agent.

The water-dispersible polyisocyanate has an average number of isocyanate groups of, for example, 2 or more, preferably 2.2 or more, and for example, 4.0 or less, preferably 3.5 or less.

The isocyanate group is contained in an amount of, for example, 5% by mass or more, preferably 7% by mass or more relative to the total amount of the water-dispersible polyisocyanate. Further, the isocyanate group is contained in an amount of, for example, 30% by mass or less, preferably 25% by mass or less, further preferably 20% by mass or less relative to the total amount of the water-dispersible polyisocyanate.

The sulfone group is contained in an amount of, for example, 0.1% by mass or more, preferably 0.2% by mass or more, more preferably 0.5% by mass or more, further preferably 1% by mass or more relative to the total amount of the water-dispersible polyisocyanate. Further, the sulfone group is contained in an amount of, for example, 10% by mass or less, preferably 5% by mass or less, more preferably 4% by mass or less, further preferably 3% by mass or less relative to the total amount of the water-dispersible polyisocyanate.

When the content ratio of the sulfone group is the above-described lower limit or more, particularly excellent water dispersibility is obtained. When the content ratio of the sulfone group is the above-described upper limit or less, particularly excellent water resistance is obtained.

The content ratio of the sulfone group can be calculated from the chemical structural formula and blending formulation in accordance with Examples to be described later.

When the water-dispersible polyisocyanate contains an oxyethylene unit, a content ratio of the oxyethylene unit to the total amount of the water-dispersible polyisocyanate is, for example, 10% by mass or less, preferably 5% by mass or less, more preferably 4% by mass or less, further preferably 3% by mass or less.

The content ratio of the oxyethylene unit can be calculated from the chemical structural formula and blending formulation in accordance with Examples to be described later.

The water-dispersible polyisocyanate has an acid value of, for example, 1 mg KOH/g or more, preferably 2 mg KOH/g or more, more preferably 3 mg KOH/g or more. Further, the water-dispersible polyisocyanate has an acid value of, for example, 56 mg KOH/g or less, preferably 34 mg KOH/g or less, more preferably 12 mg KOH/g or less.

The acid value is measured in accordance with JIS K 1557-5 (2007). Alternatively, the acid value can also be determined by calculating the sulfone group content of the water-dispersible polyisocyanate based on the charged amount of the material component.

When the acid value of the water-dispersible polyisocyanate is the above-described lower limit or more, particularly excellent water dispersibility is obtained. When the acid value of the water-dispersible polyisocyanate is the above-described upper limit or less, particularly excellent water resistance is obtained.

The above-described water-dispersible polyisocyanate contains a reaction product of the polyisocyanate component containing the bis(isocyanatomethyl)cyclohexane derivative and the hydrophilic active hydrogen component containing the sulfone group-containing active hydrogen compound. The bis(isocyanatomethyl)cyclohexane derivative contains an allophanate derivative and an isocyanurate derivative, and has an allophanate derivative content ratio within a predetermined range.

Therefore, the above-described water-dispersible polyisocyanate can obtain a polyurethane resin having excellent hardness and has excellent curability and water dispersibility.

The aqueous polyurethane resin composition contains the above-described water-dispersible polyisocyanate and an active hydrogen group-containing compound. The aqueous polyurethane resin composition may be a one-component curable polyurethane resin composition in which the water-dispersible polyisocyanate and the active hydrogen group-containing compound are mixed. The polyurethane resin composition may be a two-component curable polyurethane resin composition in which the water-dispersible polyisocyanate and the active hydrogen group-containing compound are separately prepared and blended when used.

Preferably, the aqueous polyurethane resin composition is a two-component curable polyurethane resin composition.

The two-component curable polyurethane resin composition contains the active hydrogen group-containing compound as a main component. The two-component curable polyurethane resin composition contains the above-described water-dispersible polyisocyanate as a curing agent.

The main component contains, for example, an aqueous dispersion of the active hydrogen group-containing compound.

Examples of the active hydrogen group-containing compound include macropolyols. The macropolyol is an organic compound (polymerization product) having two or more hydroxyl groups in a molecule and having a relatively high molecular weight. The macropolyol has a number average molecular weight of, for example, more than 600, and for example, 20000 or less.

Examples of the macropolyol include polyether polyol, polyester polyol, polycarbonate polyol, polyurethane polyol, epoxy polyol, vegetable oil polyol, polyolefin polyol, acrylic polyol, and vinyl monomer modified polyol. These can be used alone or in combination of two or more.

These active hydrogen group-containing compounds can be used alone or in combination of two or more.

The aqueous dispersion of the active hydrogen group-containing compound is prepared, for example, by adding water to the active hydrogen group-containing compound. Alternatively, the aqueous dispersion of the active hydrogen group-containing compound is also prepared, for example, by adding the active hydrogen group-containing compound to water.

In the aqueous dispersion of the active hydrogen group-containing compound, the content ratio of the active hydrogen group-containing compound is appropriately set in accordance with its purpose and use. For example, the active hydrogen group-containing compound (solid content) is contained in an amount of, for example, 1% by mass or more, preferably 5% by mass or more relative to the total amount of the aqueous dispersion. Further, the active hydrogen group-containing compound (solid content) is contained in an amount of, for example, 30% by mass or less, preferably 20% by mass or less relative to the total amount of the aqueous dispersion.

The curing agent contains, for example, an aqueous dispersion of the water-dispersible polyisocyanate.

The aqueous dispersion of the water-dispersible polyisocyanate is prepared, for example, by adding water to the water-dispersible polyisocyanate. Alternatively, the aqueous dispersion of the water-dispersible polyisocyanate is also prepared, for example, by adding the water-dispersible polyisocyanate to water. As necessary, a known external emulsifier can be added to water and/or the water-dispersible polyisocyanate. Alternatively, a known external emulsifier can also be added to a mixture of water and the water-dispersible polyisocyanate.

In the aqueous dispersion of the water-dispersible polyisocyanate, the content ratio of the water-dispersible polyisocyanate is appropriately set in accordance with its purpose and use. For example, the water-dispersible polyisocyanate (solid content) is contained in an amount of, for example, 1% by mass or more, preferably 5% by mass or more relative to the total amount of the aqueous dispersion. Further, the water-dispersible polyisocyanate (solid content) is contained in an amount of, for example, 30% by mass or less, preferably 20% by mass or less relative to the total amount of the aqueous dispersion.

When the aqueous dispersion of the active hydrogen group-containing compound is prepared, the aqueous dispersion of the water-dispersible polyisocyanate may not be prepared. Specifically, the solid content of the water-dispersible polyisocyanate can be used as is.

When the aqueous dispersion of the water-dispersible polyisocyanate is prepared, the aqueous dispersion of the active hydrogen group-containing compound may not be prepared. Specifically, the solid content of the active hydrogen group-containing compound can be used as is.

The aqueous polyurethane resin composition can obtain an additive. Examples of the additive include a catalyst, a solvent, an epoxy resin, a coating improver, a leveling agent, an antifoaming agent, an antioxidant, an ultraviolet absorber, a thickening agent, an anti-settling agent, a plasticizer, a surfactant, a pigment, a mildew-proofing agent, a filler, organic fine particles, and inorganic fine particles. The additive may be blended with the main component. Alternatively, the additive may be blended with the curing agent.

The amount of the additive blended is appropriately set in accordance with its purpose and use.

When the two-component curable polyurethane resin composition is used, the main component and the curing agent are blended.

The blending amounts of the main component and the curing agent are adjusted, for example, based on the equivalent ratio (isocyanate group/hydroxyl group) of the isocyanate group of the water-dispersible polyisocyanate to the active hydrogen group of the active hydrogen group-containing compound.

More specifically, an equivalent ratio (isocyanate group/active hydrogen group) of the isocyanate group of the water-dispersible polyisocyanate to the active hydrogen group of the active hydrogen group-containing compound is, for example, 0.1 or more, preferably 0.5 or more. Further, the equivalent ratio (isocyanate group/active hydrogen group) of the isocyanate group of the water-dispersible polyisocyanate to the active hydrogen group of the active hydrogen group-containing compound is, for example, 5 or less, preferably 3 or less.

The mixture of the main component and the curing agent is applied to an arbitrary object to be coated by a known coating method, and then dried under arbitrary drying conditions. Examples of the coating method include spray coating, dip coating, spin coating, rotary atomizing coating, and curtain coating.

In this manner, a coating film of the aqueous polyurethane resin composition can be formed. Thereafter, the coating film is cured by heating.

The heating conditions are appropriately set in accordance with the main component and the curing agent. For example, when the isocyanate group of the curing agent is not blocked with the blocking agent, the heating temperature is, for example, 60° C. or more, preferably 80° C. or more. Further, the heating temperature is, for example, 150° C. or less, preferably 130° C. or less. The heating time is, for example, 1 minute or more, preferably 5 minutes or more. Further, the heating time is, for example, 24 hours or less, preferably 12 hours or less.

In this manner, a polyurethane resin is obtained as a cured product of the aqueous polyurethane resin composition. Further, in this manner, an article including a coated object and a polyurethane layer is obtained. More specifically, the article includes a coated object, and a polyurethane layer disposed on a surface of the coated object, and the polyurethane layer contains a cured coating film of the above-described aqueous polyurethane resin composition. As necessary, the polyurethane resin is aged under an arbitrary condition.

When the isocyanate group of the water-dispersible polyisocyanate is blocked with the blocking agent, the aqueous polyurethane resin composition is preferably a one-component curable polyurethane resin composition. In such a case, the mixing amounts of the water-dispersible polyisocyanate and the active hydrogen group-containing compound are the same as those of the water-dispersible polyisocyanate and the active hydrogen group-containing compound in the above-described two-component curable polyurethane resin composition.

The above-described aqueous polyurethane resin composition contains the above-described water-dispersible polyisocyanate. Therefore, the above-described aqueous polyurethane resin composition can obtain a polyurethane resin having excellent hardness and is excellent in curability.

Since the above-described article includes the cured coating film of the above-described aqueous polyurethane resin composition, it has a polyurethane layer having excellent hardness.

Therefore, the above-described water-dispersible polyisocyanate, aqueous polyurethane resin composition, and article are suitably used in, for example, automobile exteriors, surface resin coats on household appliances, and flexible packaging flexo inks.

EXAMPLES

Hereinafter, the present invention will be described more in detail with reference to examples, but not limited to the examples. The specific numerical values in blending ratio (content ratio), property value, and parameter used in the following description can be replaced with upper limit values (numerical values defined as "or less" or "below") or lower limit values (numerical values defined as "or more" or "above") of corresponding numerical values in blending ratio (content ratio), property value, and parameter described in the above-described "DESCRIPTION OF THE EMBODIMENTS". The "parts" and "%" are based on mass unless otherwise specified.

Synthesis Example 1 (Preparation of Polyisocyanate A)

A four-neck flask equipped with a mixer, a thermometer, a reflux tube, and a nitrogen inlet tube was charged with 2000.0 g of 1,3-bis(isocyanatomethyl)cyclohexane (1,3-$H_6$XDI, TAKENATE 600, manufactured by Mitsui Chemicals, Inc.) and 76.4 g of isobutanol. The charged mixture was subjected to urethane-forming reaction at 80° C. for 2 hours. The equivalent ratio (NCO/OH) of the isocyanate group of 1,3-$H_6$XDI to the hydroxyl group of isobutanol was 20.

Then, as an allophanate/isocyanurate-forming catalyst, 0.52 g of DABCO-TMR (N-(2-hydroxypropyl)-N,N,N-trimethylammonium-2-ethylhexanoate, manufactured by Air Products and Chemicals, Inc.) was added to the resulting reaction solution, and the added mixture was allowed to react at temperatures of 80 to 86° C. for 2 hours.

By measuring a percentage of the isocyanate group content, it was confirmed that 10% of the isocyanate group was converted. Thereafter, 0.60 g of o-toluenesulfonic acid was added to the reaction solution to stop the reaction.

The reaction solution was distilled with a thin film distillator (degree of vacuum: 0.05 kPa, temperature: 140° C.), so that an unreacted 1,3-$H_6$XDI was removed. Thereafter, the remaining component was dissolved in propylene glycol methyl ether acetate (PMA) so as to have a solids concentration of 75.0% by mass. Thus, a polyisocyanate A was obtained.

The polyisocyanate A had an isocyanate group content (NCO %) of 13.5%.

The polyisocyanate A was measured by a gel permeation chromatography to be described later. As a result of this, it was confirmed that the polyisocyanate A contained an allophanate derivative and an isocyanurate derivative. The content of the allophanate derivative was 50% by mass of the total amount of the allophanate derivative and the isocyanurate derivative.

Synthesis Example 2 (Preparation of Polyisocyanate B)

The amount 2000.0 g of 1,3-bis(isocyanatomethyl)cyclohexane and 38.2 g of isobutanol were used. A polyisocyanate B was obtained in the same manner as in Synthesis Example 1, except those described above. The equivalent ratio (NCO/OH) of the isocyanate group of 1,3-$H_6$XDI to the hydroxyl group of isobutanol was 40.

The polyisocyanate B had an isocyanate group content (NCO %) of 13.4%. The content ratio of the allophanate derivative to the total amount of the allophanate derivative and the isocyanurate derivative was 30% by mass.

Synthesis Example 3 (Preparation of Polyisocyanate C)

The amount 2000.0 g of 1,3-bis(isocyanatomethyl)cyclohexane and 101.8 g of isobutanol were used. A polyisocyanate C was obtained in the same manner as in Synthesis Example 1, except those described above. The equivalent ratio (NCO/OH) of the isocyanate group of 1,3-$H_6$XDI to the hydroxyl group of isobutanol was 15.

The polyisocyanate C had an isocyanate group content (NCO %) of 14.5%. The content ratio of the allophanate derivative to the total amount of the allophanate derivative and the isocyanurate derivative was 70% by mass.

Synthesis Example 4 (Preparation of Polyisocyanate D)

The amount 2000.0 g of 1,3-bis(isocyanatomethyl)cyclohexane and 46.4 g of 1,3-butanediol were used. A polyisocyanate D was obtained in the same manner as in Synthesis Example 1, except those described above. The equivalent ratio (NCO/OH) of the isocyanate group of 1,3-$H_6$XDI to the hydroxyl group of 1,3-butanediol was 20.

The polyisocyanate D had an isocyanate group content (NCO %) of 14.1%. The content ratio of the allophanate derivative to the total amount of the allophanate derivative and the isocyanurate derivative was 50% by mass.

Synthesis Example 5 (Preparation of Polyisocyanate E)

The amount 2000.0 g of 1,3-bis(isocyanatomethyl)cyclohexane and 8.5 g of isobutanol were used. A polyisocyanate E was obtained in the same manner as in Synthesis Example 1, except those described above. The equivalent ratio (NCO/OH) of the isocyanate group of 1,3-$H_6$XDI to the hydroxyl group of isobutanol was 180.

The polyisocyanate E had an isocyanate group content (NCO %) of 15.2%. The content ratio of the allophanate derivative to the total amount of the allophanate derivative and the isocyanurate derivative was 10% by mass.

Synthesis Example 6 (Preparation of Polyisocyanate F)

A four-neck flask equipped with a mixer, a thermometer, a reflux tube, and a nitrogen inlet tube was charged with 1924.5 g of 1,3-bis(isocyanatomethyl)cyclohexane and 73.4 g of isobutanol. The charged mixture was subjected to urethane-forming reaction at 75° C. for 3 hours. The equivalent ratio (NCO/OH) of the isocyanate group of 1,3-$H_6$XDI to the hydroxyl group of isobutanol was 20.

Then, as an allophanate/isocyanurate-forming catalyst, 0.094 g of NEOSTANN U-600 (bismuth octoate 18% by mass, manufactured by Nitto Kasei Co., Ltd.) was added to the resulting reaction solution, and the added mixture was allowed to react at 110° C. for 18 hours. Thereafter, 0.062 g of o-toluenesulfonic acid was added thereto to stop the reaction.

The reaction solution was distilled using a thin film distillator (degree of vacuum: 0.05 kPa, temperature: 140° C.), so that an unreacted 1,3-$H_6$XDI was removed. Thereafter, the remaining component was dissolved in propylene glycol methyl ether acetate (PMA) so as to have a solids concentration of 75.0% by mass. Thus, a polyisocyanate F was obtained.

The polyisocyanate F had an isocyanate group content (NCO %) of 13.2%. The content ratio of the allophanate derivative to the total amount of the allophanate derivative and the isocyanurate derivative was 80% by mass.

Synthesis Example 7 (Preparation of Polyisocyanate G)

The amount 2000.0 g of hexamethylene diisocyanate and 2.9 g of isobutanol were used. A polyisocyanate G was obtained in the same manner as in Synthesis Example 1, except those described above. The equivalent ratio (NCO/OH) of the isocyanate group of hexamethylene diisocyanate to the hydroxyl group of isobutanol was 600.

The polyisocyanate G had an isocyanate group content (NCO %) of 17.1%.

Synthesis Example 8 (Preparation of Polyisocyanate H)

The amount 2000.0 g of 1,5-pentamethylene diisocyanate and 3.2 g of isobutanol were used. A polyisocyanate H was obtained in the same manner as in Synthesis Example 1, except those described above. The equivalent ratio (NCO/OH) of the isocyanate group of 1,5-pentamethylene diisocyanate to the hydroxyl group of isobutanol was 600.

The polyisocyanate H had an isocyanate group content (NCO %) of 18.5%.

Synthesis Example 9 (Preparation of Polyisocyanate I)

VESTANAT T-1890 (isophorone diisocyanate trimer, manufactured by Evonik) was prepared. This was determined as a polyisocyanate I.

<Gel Permeation Chromatography (GPC)>

The molecular weight distribution of each of the polyisocyanates was measured with the following GPC system.

The area ratio of a peak corresponding to the allophanate derivative to all the peaks was determined as a percentage of the allophanate derivative content. The area ratio of the remaining peaks to all the peaks was determined as a percentage of the isocyanurate derivative content.

When the isobutanol is used, a peak having a peak top in a molecular weight range of 410 to 510 is the peak corresponding to the allophanate derivative. When the 1,3-butanediol is used, a peak having a peak top in a molecular weight range of 770 to 870 is the peak corresponding to the allophanate derivative.

Gpc System:

Apparatus used: HCL-8020 (manufactured by Tosoh Corporation)

Column used: G1000HXL, G2000HXL, and G3000HXL (trade names, hereinabove manufactured by Tosoh Corporation) serially connected Sample concentration: 0.3% by mass, tetrahydrofuran solution Sample injection volume: 100 μL Eluent: Tetrahydrofuran Flow rate of eluent: 0.8 ml/min Column temperature: 40° C.

Detection method: Differential refractive index

Standard substance: Polyethylene oxide (trade name: TSK standard polyethylene oxide, manufactured by Tosoh Corporation)

Examples 2 to 9 and Comparative Examples 1 to 6

A water-dispersible polyisocyanate was obtained according to the formulation shown in Tables 1 to 2.

More specifically, the polyisocyanate component and the hydrophilic active hydrogen component were mixed and allowed to react with each other at temperatures of 80 to 90° C. for 8 hours under dry nitrogen. Thereafter, a neutralizing agent was added to the reaction mixture, and a solvent was further added thereto to adjust the solids concentration.

Example 10

A water-dispersible polyisocyanate in which isocyanate groups had been blocked was obtained according to the formulation shown in Table 3.

More specifically, the polyisocyanate component and the hydrophilic active hydrogen component were mixed and allowed to react with each other at temperatures of 80 to 90° C. for 8 hours under dry nitrogen. Thereafter, a neutralizing agent was added thereto. Further, dimethylpyrazole was added to the reaction mixture and allowed to react at temperatures of 40 to 50° C. Thereafter, the reaction mixture was stirred for 2 hours until the isocyanate group (2260 $cm^{-1}$) was not detected by an IR spectrometer. In this manner, the isocyanate group was blocked with the dimethylpyrazole.

Thereafter, the reaction mixture that had been cooled to 30° C. was slowly added to stirred deionized water.

Thus, an aqueous dispersion of the water-dispersible polyisocyanate in which the isocyanate groups had been blocked was obtained.

<Acid Value (mg KOH/g)>

An acid value of the water-dispersible polyisocyanate was measured in accordance with JIS K 1557-5 (2007).

<Content Ratio of Sulfone Group ($SO_3$ Content, Mass %)>

The content ratio of the sulfone group (percentage of $SO_3$ content) in the water-dispersible polyisocyanate was calculated as $SO_3$ equivalent with a molecular weight of 80 from the chemical structural formula and blending formulation.

<Content Ratio of Oxyethylene Unit (EO Content, Mass %)>

The content ratio of an ethylene oxide unit was calculated from the chemical structural formula and blending formulation by the following expression.

((Molecular weight of methoxy PEG−32)/molecular weight of methoxy PEG)×charged amount of methoxy PEG/amount of resin)×100

<Content Ratio of Isocyanate Group (NCO Content, Mass %)>

The content ratio of the isocyanate group was measured by n-dibutylamine titration method in accordance with JIS K-1556 (2006), using a potentiometric titrator.

Evaluation (1) Water Dispersibility

The amount 5 g of the solid content of the water-dispersible polyisocyanate was added to 95 g of water. The resulting mixture was stirred with a magnetic stirrer for 15 minutes, and then allowed to stand for 1 hour. The properties of the liquid mixture were evaluated by the following evaluation criteria.

Good: No precipitate appeared.

Fair: Precipitate appeared, but can be redispersed by stirring.

Bad: Precipitate appeared and cannot be redispersed.

(2) Hardness

An aqueous acrylic emulsion (solids concentration: 40.0% by mass) having a hydroxyl value of 50 mg KOH/g was diluted with water so as to adjust the solids concentration to 25% by mass. This aqueous solution was determined as a main component.

Each of the water-dispersible polyisocyanates as a curing agent was added to the above-described main component and then stirred for 15 minutes. The equivalent ratio (NCO/OH) of the isocyanate group in the curing agent to the hydroxyl group in the main component was set to 1.0.

Thereafter, the liquid mixture of the main component and the curing agent was applied onto a glass plate. The application amount was adjusted so as to have a dried thickness of 20 μm. Thereafter, the coated film was dried at 110° C. for 30 minutes and aged at 23° C. for 7 days. In this manner, a cured film was obtained.

König's hardness of the cured film was measured at 23° C. by a pendulum hardness tester available from BYK. The hardness was evaluated by the following evaluation criteria.

Good: 70 or more

Fair: 60 or more and less than 70

Bad: Less than 60

(3) Curability

An aqueous acrylic emulsion (solids concentration: 40.0% by mass) having a hydroxyl value of 50 mg KOH/g was diluted with water so as to adjust the solids concentration to 25% by mass. This aqueous solution was determined as a main component.

Each of the water-dispersible polyisocyanates as a curing agent was added to the above-described main component and then stirred for 15 minutes. The equivalent ratio (NCO/OH) of the isocyanate group in the curing agent to the hydroxyl group in the main component was set to 1.0.

Thereafter, the liquid mixture of the main component and the curing agent was applied onto a glass plate. The application amount was adjusted so as to have a dried thickness of 20 μm. Thereafter, the coated film was dried at 110° C. for 30 minutes and aged at 23° C. for 7 days. In this manner, a cured film was obtained.

The cured film was immersed in a liquid mixture of acetone and methanol (mass ratio 1:1) for 24 hours.

The residual ratio of the cured film after immersion was calculated and then evaluated by the following evaluation criteria.

Good: Residual ratio being 90% or more

Fair: Residual ratio being 80% or more and less than 90%

Bad: Residual ratio being less than 80%

(4) Elasticity

First, the cured film obtained by the method of evaluation (2) was cut into a size having a width of 5 mm and a length of 10 cm. In this manner, a sample was obtained.

Then, the storage modulus of the sample at 0° C. was measured by the following method.

Specifically, a dynamic mechanical analyzer (model: RSA-III, manufactured by TA Instruments) was used. The measurement conditions were set as follows.

Measurement Atmosphere: Nitrogen

Measurement mode: Tension mode (Auto tension, Auto strain control)

Measurement Temperature: −50 to 200° C.

Heating rate: 5° C./min

Frequency: 10 Hz

The evaluation criteria are shown below.

Good: $1.5\times10^9$ Pa or more

Bad: Less than $1.5\times10^9$ Pa

TABLE 1

| No. | | | Example 1 | Example 2 | Example 3 | Example 4 | Example 5 | Example 6 | Example 7 | Example 8 | Example 9 |
|---|---|---|---|---|---|---|---|---|---|---|---|
| Water-disperible polyisocyanate | | | A | B | C | D | B | F | G | H | I |
| Polyisocyanate component | Polyisocyanate (pts. mass) | A | 728.5 | — | — | 711.4 | 455.9 | — | 732.5 | 657.9 | 623.1 |
| | | B | — | 728.7 | — | — | — | — | — | — | — |
| | | C | — | — | 728.7 | — | — | — | — | — | — |
| | | D | — | — | — | — | — | 728.7 | — | — | — |
| | | E | — | — | — | — | — | — | — | — | — |
| | | F | — | — | — | — | — | — | — | — | — |
| | | G | — | — | — | — | 360.4 | — | — | — | — |
| | | H | — | — | — | — | — | — | — | — | — |
| | | I | — | — | — | — | — | — | — | — | — |
| | Type of isocyanate | | $H_6XDI$ | $H_6XDI$ | $H_6XDI$ | $H_6XDI$ | $H_6XDI$ + HDI | $H_6XDI$ | $H_6XDI$ | $H_6XDI$ | $H_6XDI$ |
| | Type of alchol | | IBA | IBA | IBA | IBA | IBA | 1,3-BG | IBA | IBA | IBA |
| | Allophanate in $H_6XDI$ denvative (mass %) | | 50 | 70 | 30 | 50 | 50 | 50 | 50 | 50 | 50 |
| Hydrophilic active hydrogen component (pts. mass) | CAPS | | 18.2 | 18.0 | 18.0 | 8.4 | 20.1 | 18.0 | 14.8 | 77.9 | 107.3 |
| | MePEG1000 | | — | — | — | 38.1 | — | — | — | — | — |
| Neutralizing agent (pts. mass) | DMCHA | | 10.5 | 10.4 | 10.4 | 4.9 | 11.6 | 10.4 | 8.5 | 44.9 | 61.8 |
| Solvent (pts. mass) | PMA | | 242.8 | 242.9 | 242.9 | 237.1 | 152.0 | 242.9 | 244.2 | 219.3 | 207.7 |
| Properties | Solid content | mass % | 76 | 76 | 76 | 76 | 85 | 76 | 76 | 78 | 79 |
| | Acid value | mg KOH/g | 6.1 | 6 | 5 | 2.9 | 6.0 | 6.0 | 5.0 | 25.3 | 34.4 |
| | $SO_3$ content | mass % | 0.9 | 0.9 | 0.9 | 0.4 | 0.9 | 0.9 | 0.7 | 3.6 | 4.9 |
| | EO content | mass % | — | — | — | 3.8 | — | — | — | — | — |
| | NCO content | mass % | 12.8 | 12.7 | 12.3 | 12.5 | 16.0 | 13.4 | 12.9 | 10.4 | 9.2 |
| Evaluation | Water dispersibility | | Good | Good | Fair | Good | Good | Fair | Fair | Good | Good |
| | Hardness | | Good | Fair | Good | Good | Fair | Good | Good | Good | Good |
| | Curability | | Good | Good | Good | Good | Good | Good | Good | Good | Good |
| | Elasticity | | Good | Good | Good | Good | Good | Good | Good | Good | Good |
| | Water resistance | | Good | Good | Good | Good | Good | Good | Good | Good | Fair |

| No. | | | Comp. Ex. 1 | Comp. Ex. 2 | Comp. Ex. 3 | Comp. Ex. 4 | Comp. Ex. 5 |
|---|---|---|---|---|---|---|---|
| Water-disperible polyisocyanate | | | J | K | L | N | O |
| Polyisocyanate component | Polyisocyanate (pts. mass) | A | — | — | — | — | — |
| | | B | — | — | — | — | — |
| | | C | — | — | — | — | — |
| | | D | — | — | — | — | — |

-continued

| No. | | | Comp. Ex. 1 | Comp. Ex. 2 | Comp. Ex. 3 | Comp. Ex. 4 | Comp. Ex. 5 |
|---|---|---|---|---|---|---|---|
| | E | | — | — | — | 728.7 | — |
| | F | | — | — | — | — | 729.0 |
| | G | | 722.2 | — | — | — | — |
| | H | | — | 722.1 | — | — | — |
| | I | | — | — | 705.3 | — | — |
| | Type of isocyanate | | HDI | PDI | IPDI | $H_6XDI$ | $H_6XDI$ |
| | Type of alchol | | IBA | IBA | IBA | IBA | IBA |
| | Allophanate in $H_6XDI$ denvative (mass %) | | 0 | 0 | 50 | 10 | 80 |
| Hydrophilic active hydrogen component (pts. mass) | CAPS | | 17.7 | 17.7 | 37.9 | 18.0 | 17.8 |
| | MePEG1000 | | — | — | — | — | — |
| Neutralizing agent (pts. mass) | DMCHA | | 10.2 | 10.2 | 21.8 | 10.4 | 10.2 |
| Solvent (pts. mass) | PMA | | 250.0 | 250.0 | 235.1 | 242.9 | 243.0 |
| Properties | Solid content | mass % | 75 | 75 | 60 | 76 | 76 |
| | Acid value | mg KOH/g | 6.0 | 6.0 | 12.5 | 6 | 6 |
| | $SO_3$ content | mass % | 0.9 | 0.9 | 1.8 | 0.9 | 0.9 |
| | EO content | mass % | — | — | — | — | — |
| | NCO content | mass % | 16.1 | 17.5 | 9.4 | 14.4 | 12.5 |
| Evaluation | Water dispersibility | | Good | Good | Bad | Bad | Good |
| | Hardness | | Bad | Bad | Fair | Good | Bad |
| | Curability | | Good | Good | Bad | Fair | Good |
| | Elasticity | | Good | Good | Good | Good | Good |
| | Water resistance | | Good | Good | Good | Good | Fair |

TABLE 3

| No. Water-dispersible polyisocyanate | | | Example 10 P |
|---|---|---|---|
| Polyisocyante component | Polyisocyanate (pts. mass) | A | 541.0 |
| | | B | — |
| | | C | — |
| | | D | — |
| | | E | — |
| | | F | — |
| | | G | — |
| | | H | — |
| | | I | — |
| | Type of isocyante | | $H_6XDI$ |
| | Type of alcohol | | IBA |
| | Allophanate in $H_6XDI$ derivative (mass %) | | 50 |
| Hydrophilic active hydrogen component (pts. mass) | CAPS | | 48.8 |
| Blocking agent (pts. mass) | Dimethylpyrazole | | 201.7 |
| Neutralizing agent (pts. mass) | DMCHA | | 28.1 |
| Solvent (pts. mass) | PMA | | 1912.5 |
| Properties | Solid content | mass % | 30 |
| | Acid value | mg KOH/g | 20 |
| | $SO_3$ content | mass % | 2.9 |
| | EO content | mass % | — |
| | INCO content | mass % | 8.8 |

The details of the abbreviations in Tables are given in the following.

$H_6XDI$: 1,3-bis(isocyanatomethyl)cyclohexane, TAKENATE 600, Manufactured by Mitsui Chemicals, Inc.

HDI: 1,6-hexamethylene diisocyanate

PDI: 1,5-pentamethylene diisocyanate

IPDI: Isophorone diisocyanate

IBA: Isobutanol 1,3-BG: 1,3-butanediol

CAPS: 3-(cyclohexylamino)-propanesulfonic acid, sulfone group-containing active hydrogen compound MePEG 1000: Methoxy PEG, one-end-capped polyoxyethylene glycol, nonion group-containing active hydrogen compound, number average molecular weight 1000

DMCHA: N,N-dimethylcyclohexylamine

PMA: Propylene glycol methyl ether acetate

While the illustrative embodiments of the present invention are provided in the above-described invention, such is for illustrative purpose only and it is not to be construed restrictively. Modification and variation of the present invention that will be obvious to those skilled in the art is to be covered by the following claims.

INDUSTRIAL APPLICABILITY

The water-dispersible polyisocyanate, aqueous polyurethane resin composition, and article according to the present invention are suitably used in, for example, automobile exteriors, surface resin coats on household appliances, and flexible packaging flexo inks.

The invention claimed is:

1. A water-dispersible polyisocyanate, being a water-dispersible polyisocyanate comprising an isocyanate group and a sulfone group, comprising a reaction product of a polyisocyanate component and a hydrophilic active hydrogen component, the polyisocyanate component comprising a bis(isocyanatomethyl)cyclohexane derivative, the hydrophilic active hydrogen component comprising a sulfone group-containing active hydrogen compound, the bis(isocyanatomethyl)cyclohexane derivative comprising an allophanate derivative and an isocyanurate derivative, wherein the allophanate derivative is contained in an amount of 25% by mass or more and 75% by mass or less relative to a total amount of the allophanate derivative and the isocyanurate derivative.

2. The water-dispersible polyisocyanate according to claim 1, wherein the bis(isocyanatomethyl)cyclohexane derivative comprises a reaction product of a bis(isocyanatomethyl) cyclohexane monomer and an alcohol, and the alcohol comprises a monool.

3. The water-dispersible polyisocyanate according to claim 1, wherein the sulfone group is contained in an amount of 0.2% by mass or more and 5% by mass or less relative to a total amount of the water-dispersible polyisocyanate.

4. The water-dispersible polyisocyanate according to claim 1, wherein the isocyanate group of the water-dispersible polyisocyanate is blocked with a blocking agent.

5. An aqueous polyurethane resin composition comprising:

the water-dispersible polyisocyanate according to claim 1; and an active hydrogen group-containing compound.

6. An article, comprising:

a coated object; and a polyurethane layer disposed on a surface of the coated object, wherein the polyurethane layer comprises a cured coating film of the aqueous polyurethane resin composition according to claim 5.

* * * * *